United States Patent [19]

Collins

[11] 4,182,729

[45] Jan. 8, 1980

[54] ARYLVINYL CYCLOPROPYL KETONES

[75] Inventor: Joseph C. Collins, East Greenbush, N.Y.

[73] Assignee: Sterling Drug Inc., New York, N.Y.

[21] Appl. No.: 885,575

[22] Filed: Mar. 13, 1978

Related U.S. Application Data

[60] Division of Ser. No. 740,358, Nov. 10, 1976, Pat. No. 4,093,736, which is a continuation-in-part of Ser. No. 545,486, Jan. 30, 1975, which is a continuation-in-part of Ser. No. 436,611, Jan. 25, 1974, Pat. No. 3,917,718, which is a continuation-in-part of Ser. No. 265,333, Jun. 22, 1972, Pat. No. 3,829,475.

[30] Foreign Application Priority Data

Jun. 18, 1973 [GB] United Kingdom ............... 28793/73

[51] Int. Cl.$^2$ .................... C07C 49/84; C07D 317/06
[52] U.S. Cl. .......................... 260/590 C; 260/340.5 R
[58] Field of Search .................... 260/590 C, 340.5 R

[56] References Cited

U.S. PATENT DOCUMENTS

| | | | |
|---|---|---|---|
| 3,458,565 | 7/1969 | Bicking | 260/590 C |
| 3,878,200 | 4/1975 | Diana et al. | 260/590 C |
| 4,005,103 | 1/1977 | Teulon | 260/590 C |

*Primary Examiner*—James H. Reamer
*Attorney, Agent, or Firm*—Thomas L. Johnson; B. Woodrow Wyatt

[57] ABSTRACT

Aryl substituted diketones and keto-esters, useful as antiviral agents and insecticides, are prepared by reacting an arylalkyl or arylalkenyl iodide with a metal salt of the appropriate diketone or keto-ester. The intermediate iodides are prepared by condensing a methyl cyclopropyl ketone with an aromatic aldehyde to give an arylvinyl cyclopropyl ketone, reducing the latter to an arylethyl cyclopropyl carbinol or arylvinyl cyclopropyl carbinol, treating the carbinol with phosphorus tribromide and then with zinc bromide to give an arylalkyl or arylalkenyl bromide, and then replacing the bromine atom by iodine.

7 Claims, No Drawings

ARYLVINYL CYCLOPROPYL KETONES

This application is a division of copending application Ser. No. 740,358, filed Nov. 10, 1976, now U.S. Pat. No. 4,093,736, which in turn is a continuation-in-part of copending application Ser. No. 545,486, filed Jan. 30, 1975, which in turn is a continuation-in-part of copending application Ser. No. 436,611, filed Jan. 25, 1974, now U.S. Pat. No. 3,917,718, which in turn is a continuation-in-part of application Ser. No. 265,333, filed June 22, 1972, now U.S. Pat. No. 3,829,475.

This application relates to aryl substituted diketones and keto-esters, to the preparation thereof and to certain novel intermediates.

The compounds of the invention are of the structural formula

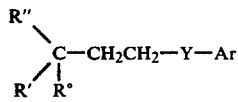

wherein Y is selected from the group consisting of:

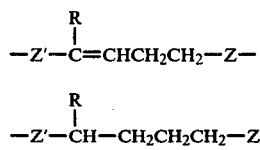

and $-Z'-\underset{\underset{R}{|}}{C}=CHCH=CH-Z-$;

R' is lower-alkanoyl of 2 to 6 carbon atoms;
R" is lower-alkanoyl of 2 to 6 carbon atoms or carbo-lower-alkoxy of 2 to 6 carbon atoms;
R° is hydrogen, lower-alkyl of 1 to 4 carbon atoms or chloro;
R is hydrogen or lower-alkyl of 1 to 4 carbon atoms;
Z is a single bond, vinylene (only when the remainder of Y is unsaturated) or ethylene (only when Y is saturated);
Z' is a single bond, methylene or ethylene; and
Ar is phenyl, naphthyl or phenyl substituted by 3,4-methylenedioxy or from one to three monovalent substituents selected from the group consisting of lower-alkyl of 1 to 4 carbon atoms, lower-alkoxy of 1 to 4 carbon atoms, carbo-lower-alkoxy of 2 to 4 carbon atoms, halogen, nitro, trifluoromethyl, trifluoromethoxy, hydroxy, acyloxy of 1 to 10 carbon atoms, benzyloxy, alkanoylamino of 1 to 4 carbon atoms, dialkylamino where alkyl has from 1 to 4 carbon atoms, and aminosulfonyl.

The carbon chains of R, R', R", R° and Ar substituents can be straight or branched, although primary or secondary alkyl moieties are preferred.

When two or three monovalent substituents are present on the phenyl ring of Ar, they can be the same or different.

The compounds of the invention where Z and Z' are both single bonds and R° is hydrogen are prepared as described in the following Reaction Sequences A and B.

Reaction Sequence A

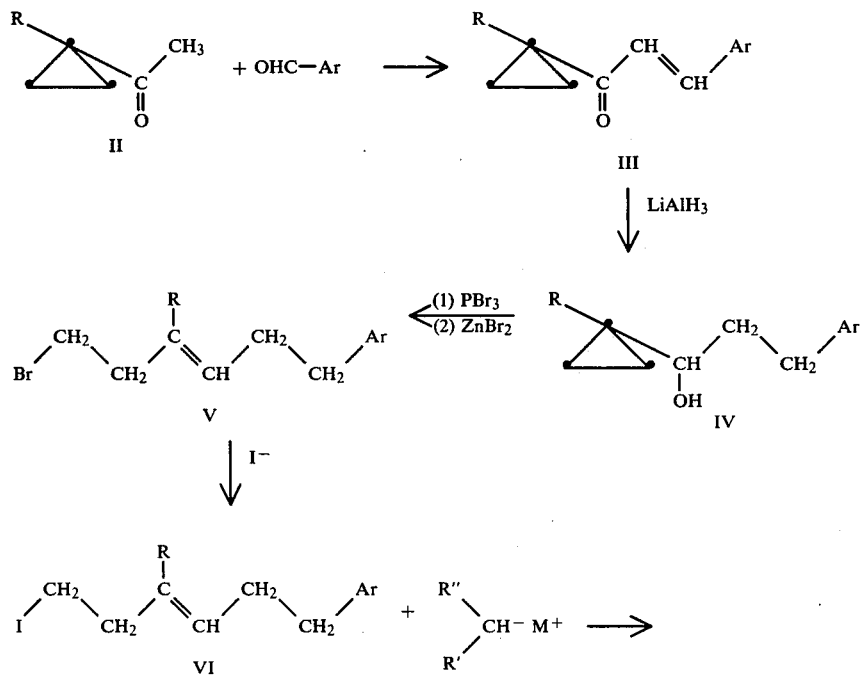

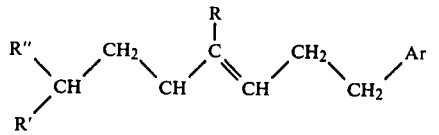

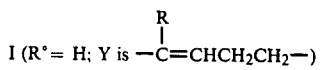

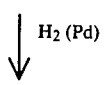

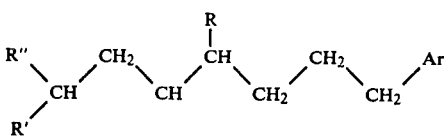

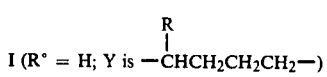

In the foregoing Reaction Sequence A, a 1-R-1-acetylcyclopropane of formula II, where R has the meaning given hereinabove, is treated with an aldehyde ArCHO in the presence of a base to give the arylvinyl 1-R-cyclopropyl ketone of formula III. The latter, when treated with an alkali metal aluminum hydride, preferably lithium aluminum hydride, is reduced at both the carbonyl group and the olefinic linkage to give an arylethyl 1-R-cyclopropyl carbinol of formula IV. This carbinol is then treated with phosphorus tribromide in the presence of a metal bromide such as lithium bromide to replace the hydroxy group by bromine, which product is then treated with zinc bromide to effect ring opening to form an arylalkenyl bromide of formula V. The latter with a metallic iodide is converted to the corresponding iodide of formula VI. The iodide then is treated with the alkali metal enolate salt of a diketone or keto-ester of formula (R')(R'')CH⁻M⁺, where R' and R'' have the meanings given hereinabove and M⁺ is an alkali metal, preferably lithium, sodium or potassium. The reaction takes place in an inert solvent under anhydrous conditions and produces a compound of formula I where R° is hydrogen and Y is —C(R)=CHCH₂CH₂—. Catalytic hydrogenation of the latter, for example with palladium, platinum or rhodium catalyst, reduces the olefinic linking to afford a compound of formula I where R° is hydrogen and Y is —CH(R)CH₂CH₂CH₂—.

Alternatively, hydrogenation of the double bond may be performed earlier in the synthesis, upon the unsaturated bromide of formula V. Hydrogenation of the latter in the presence of palladium or platinum oxide catalyst produces a saturated bromide of formula

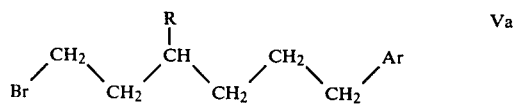

Reaction Sequence B

The latter in turn is converted to the corresponding iodide:

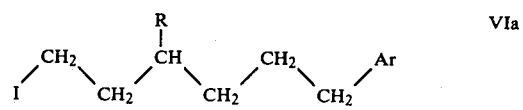

which then is treated with the metallo derivative (R')(R'')CH⁻M⁺ to give I (R° is H; Y is —CH(R)CH₂CH₂CH₂).

It has also been found that saturated bromides of formula Va can be caused to react directly with the metallo derivative (R')(R'')CH⁻M⁺, without intermediate conversion to the iodides VIa, to form final products of formula I. The iodide reaction takes place at temperatures of 20°–60° C., whereas the bromide reaction requires a higher temperature, about 100°–150° C.

In the event that one or more nitro groups are present in the aromatic nucleus, double bond reductions are carried out by an alternative method in order to avoid reduction of the nitro group(s). This alternative method comprises treating the olefinic compounds with hydroxylamine and hydroxylamine O-sulfonic acid in sodium hydroxide solution [Dürckheimer, Annalen 721, 240 (1969)].

A further alternative approach to compounds within the scope of the present invention involves a Friedel-Crafts type reaction between an aromatic compound, ArH, and an omega-haloalkanoic acid halide. The carbonyl group of the resulting aromatic ketone is subsequently removed by reductive methods to give an arylaliphatic halide which is converted to the compounds of the invention by procedures already described.

-continued

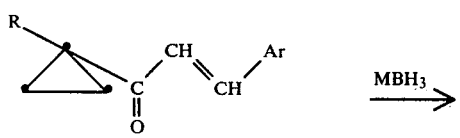 MBH₃ → 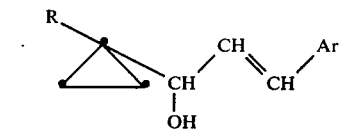

VII

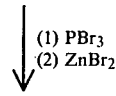
(1) PBr₃
(2) ZnBr₂

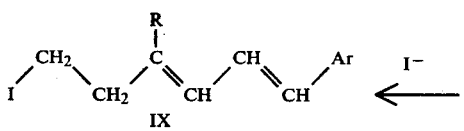 I⁻ ⟵ 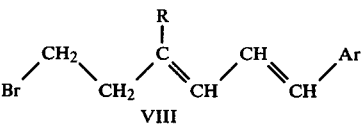
IX                                         VIII

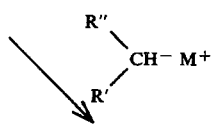

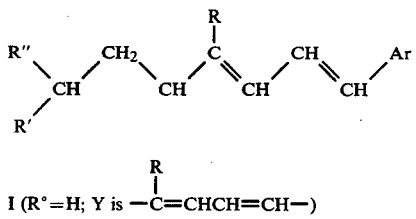

I (R°=H; Y is —C(R)=CHCH=CH—)

In Reaction Sequence B the arylvinyl 1-R-cyclopropyl ketone of formula III is treated with an alkali metal borohydride, preferably sodium borohydride to reduce the carbonyl group but not the olefinic linkage and provide an arylvinyl 1-R-cyclopropyl carbinol of formula VII. By procedures analogous to those shown in Reaction Sequence A, the carbinol of formula VII is treated with phosphorus tribromide in the presence of a metal bromide and then with zinc bromide to give a diunsaturated aralkyl bromide of formula VIII. The latter is then converted to the corresponding iodide (IX), which reacts with the alkali metal enolate salt of a diketone or keto-ester to afford a compound of formula I where R° is hydrogen and Y is —C(R)=CHCH=CH—. If desired, the latter can be catalytically hydrogenated to produce a compound of formula I where Y is —CH(R)CH₂CH₂CH₂—.

In the event that compounds of formula I where the variable Z defined above is vinylene (—CH=CH—) are desired, the same reaction sequence as in A can be carried out starting with cinnamaldehyde or a substituted cinnamaldehyde of the formula OHC—CH=CH—Ar.

Also, the first step of Reaction Sequence A can be used to produce the corresponding aryl-CH=CH-vinyl 1-R-cyclopropyl ketone for similar use as the starting material in Reaction Sequence B. Catalytic hydrogenation of the compounds where Z is vinylene affords the compounds where Z is ethylene.

If it is desired to obtain compounds of formula I wherein Ar is substituted by from one to three hydroxy groups, the reaction sequences can be carried out with the corresponding compounds where Ar is substituted by from one to three benzyloxy groups. The benzyloxy group or groups can then be cleaved by catalytic hydrogenolysis. Any unsaturated linkages in the aliphatic bridge are also hydrogenated at the same time. Alternatively, if it is desired to obtain compounds where Ar is substituted by one or more free hydroxy groups and where the aliphatic bridge is unsaturated, the hydroxy group(s) can be protected throughout the syntheses by esterification (as acetate or benzoate), and the ester hydrolyzed as the final step. The ester protection method is of course also applicable to the preparation of compounds where the aliphatic bridge is saturated.

It is not, however, essential that phenolic hydroxy groups be protected in the form of esters or ethers at the final step of the synthesis because the diketone or keto ester reactant, R'CH₂R" is more acidic than the phenolic hydroxyl; hence the desired alkylation with the iodides or bromides (VI, VIa, Va) will take place without affecting any phenolic hydroxy groups which may be present.

The compounds of formula I where the aryl group is substituted by acyloxy can also be prepared by conventional esterification of the corresponding hydroxy compounds of formula I with the appropriate acid, acid halide or acid anhydride. The acyloxy groups are derived from carboxylic acids having from one to about ten carbon atoms, and having a molecular weight less than about 200. Representative of the acyl radicals which can be present are lower-alkanoyl radicals, e.g., formyl, acetyl, propionyl, butyryl, isobutyryl, caproyl, heptanoyl, octanoyl, trimethylacetyl, and the like; carboxy-lower-alkanoyl radicals, e.g., succinyl (β-carboxypropionyl); cycloalkyl-lower-alkanoyl radicals, e.g., β-cyclopentylpropionyl, β-cyclohexylpropionyl, and the like; monocarbocyclic aroyl radicals, e.g., benzoyl, p-toluyl, p-nitrobenzoyl, 3,4,5-trimethoxybenzoyl, and the like; monocarbocyclic aryl-lower-alkanoyl or -alkenoyl radicals, such as phenylacetyl, β-phenylpropionyl, cinnamoyl, and the like; monocarbocyclic aryloxy-lower-alkanoyl radicals, such as p-chlorophenoxyacetyl, and the like; and amino-lower-alkanoyl, such as glycinyl, alaninyl, morpholinobutyryl, and the like. When monocarbocyclic aryl groups are present in the ester moieties, monocarbocyclic aryl includes phenyl and phenyl substituted by from one to three lower-alkyl, lower-alkoxy, halogen or nitro groups.

In the reaction of the arylalkyl iodides or arylalkenyl iodides of formulas VI or IX with the lithium enolate salt of a diketone or keto-ester, some of the iodide reactant undergoes dehydrohalogenation to produce a compound of the formula $$CH_2=CH-Y-Ar \qquad \text{X}$$

The byproducts of formula X are readily separated from the main products of formula I by chromatographic procedures, because the former are of more non-polar character than the latter. Selected compounds of formula X having the structure

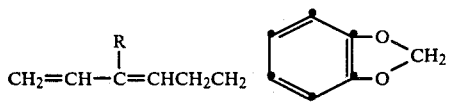

Xa when R is lower-alkyl of 1–4 carbon atoms have been isolated and characterized and are within the purview of the invention. The dehydrohalogenation reaction occurs in the presence of any basic reagent.

The compounds of formula I when R° is chloro can be prepared by treating the corresponding compounds of formula I when R° is hydrogen with a chlorinating agent. An appropriate chlorinating agent is one which introduces a chlorine atom in a position alpha to a carbonyl group. Examples of appropriate chlorinating agents are t-butyl hypochlorite, cupric chloride and sulfuryl chloride.

The compounds of formula I where R° is lower-alkyl can be prepared by treating the corresponding compounds of formula I where R° is hydrogen with a lower-alkyl iodide in the presence of a strong base under anhydrous conditions. The strong base can be an alkali metal alkoxide, hydride or amide, or a strong organic amine such as 1,5-diazabicyclo[5.4.0]undec-5-ene.

The compounds of formula I above where Z' is $CH_2$ or $CH_2CH_2$ are prepared by homologation reactions carried out on the intermediate iodides (formulas VI, VIa, IX). For one-carbon homologation (Z' is $CH_2$), the iodide is interacted with thioanisole and phenyllithium to produce a phenyl thioether where the iodine atom is replaced by $C_6H_5SCH_2$. The phenyl thioether is then heated with methyl iodide which replaces the $C_6H_5S$ group by iodine, yielding the next higher homolog of the original iodide.

For two-carbon homologation (Z' is $CH_2CH_2$), the intermediate iodide of formula VI, VIa or IX is condensed with an alkali metal salt of a malonic ester to give a compound of the formula

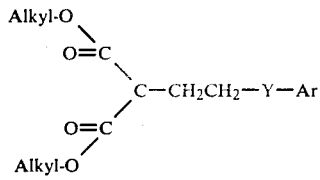

XI

The compound of formula XI is then hydrolyzed and decarboxylated with aqueous alkali to produce a monobasic acid (XII):

$$HOOC-CH_2CH_2CH_2-Y-Ar \qquad \text{XII}$$

Lithium-aluminum hydride reduction of the latter acid converts it to the alcohol (XIII):

$$HOCH_2CH_2CH_2CH_2-Y-Ar \qquad \text{XIII}$$

The latter alcohol is converted to the corresponding iodide by treating its p-toluenesulfonate ester with sodium iodide. The iodide, when condensed with the alkali metal salt of a diketone or keto ester, $(R')(R'')CH^-M^+$, affords compounds of formula I where Z' is $CH_2CH_2$.

A further and preferred aspect of the invention resides in compounds of the formula

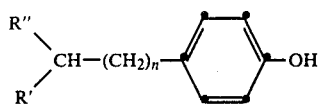

XIV wherein R' and R'' are lower-alkanoyl of 2–6 carbon atoms and n is an integer from 4 to 8, inclusive. The compounds where n is 6–8 can be prepared by methods already described. The compounds where n is 4–5, as well as the compounds where n is 6–8, can be prepared by an alternative synthetic approach starting with anisole. Anisole is subjected to a Friedel-Crafts reaction with an acid halide of the formula $X'(CH_2)_{n-1}COX'$ where X' is chlorine or bromine to give a halo-ketone of the formula $X'(CH_2)_{n-1}COC_6H_4OCH_3(-p)$. The latter is catalytically reduced to a haloalkyl substituted anisole, $X'(CH_2)_nC_6H_4OCH_3(-p)$, which is then converted to the iodide, $I(CH_2)_nC_6H_4OCH_3(-p)$ and demethylated to the phenol, $I(CH_2)_nC_6H_4OH(-p)$. The latter with an alkali metal salt of a diketone R'$CH_2$R'' produces a compound of formula XIV. In the event X' in the compound $X'(CH_2)_nC_6H_4OCH_3(-p)$ is bromine the conversion to the iodide and the demethylation can occur simultaneously by using hydriodic acid.

Biological evaluation of the compounds of formula I and XIV has shown that they possess antiviral activity. They have been found to be effective against one or more of a large variety of RNA and DNA viruses, including Myxoviruses, e.g. influenza types $A_0$, $A_1$, A-2, B; Paramyxoviruses, e.g. parainfluenza types 1, 2, 3, and mumps virus; Picornaviruses, e.g. human rhinoviruses, Coxsackie viruses types A, B, ECHO viruses, equine rhinoviruses; Reoviruses, types 1, 2, 3; Arboviruses, e.g. equine encephalomyelitis (Eastern, Western and Venezuelan), Semliki Forest virus; miscellaneous RNA viruses, e.g. measles, distemper, respiratory syncytial, rubella, vesicular stomatitis, hepatitis; Herpes viruses, e.g. HSV type I, II, herpesvirus simiae, herpesvirus varicellae, infectious bovine rhinotracheitis, cytomegalovirus, Marek's disease virus, Epstein-Barr virus; Poxviruses, e.g. variola, vaccinia; leukemogenic viruses. Both in vitro and in vivo antiviral activity have been found in the compounds of the invention. The in vitro testing of the compounds showed that they had minimal growth inhibitory concentrations (mic) ranging from about 0.3 to about 50 micrograms per milliliter. The mic values were determined by standard serial dilution procedures. Certain of the intermediates of formulas III, IV and VII also showed antiviral activity.

The compounds of formulas I and Xa have also been found to possess pesticidal activity. They showed juvenile hormone-like activity when tested under simulated field conditions in a greenhouse against one or more of the following pest species: yellow mealworm pupae, dock beetle larvae, cabbage looper larvae, yellow fever mosquito larvae and rhodnius prolixus nymph.

The structures of the compounds of the invention were established by the modes of synthesis, by elementary analysis, and by infrared and nuclear magnetic resonance spectral determinations.

A further aspect of the invention relates to compositions for combatting arthropods by hindering the maturation thereof which comprise an effective amount of at least one compound of formula I in admixture with a suitable carrier or diluent, and to the method of combatting arthropods at any stage of their development by contacting them with said compositions.

The compositions of the invention are effective against insects at any stage of their development short of the final adult form, i.e. at the egg, larval or pupal stages. The compounds can be formulated in conventional manner as solutions, emulsions, suspensions, dusts and aerosol sprays. The pesticide compositions of the invention can contain adjuvants found normally in such preparations, including water and/or organic solvents such as acetone, dimethylformamide, sesame oil, petroleum oils, and the like. Emulsifying and surface active agents may also be added. Dust formulations can contain talc, diatomaceous earth, kaolin, bentonite, calcium carbonate, wood, flour, cork, carbon, and the like. The aerosol sprays contain propellants such as dichlorodifluoromethane. The compounds of this invention can be employed as the sole pesticide component or they can be used in admixture with other compounds having similar utility. While the concentration of active ingredient can vary within rather wide limits, ordinarily the pesticide will comprise not more than about 10%, and preferably about 1% by weight of the composition.

A still further aspect of the invention relates to compositions for combatting viruses which comprise an antivirally effective amount of at least one compound of formula I in admixture with a suitable carrier or diluent, and to the method of combatting viruses by contacting the locus of said viruses with said compositions.

The antiviral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams.

The following examples will further illustrate the invention.

PREPARATION OF INTERMEDIATES

A. 2-Arylvinyl cyclopropyl ketones (III)

A1. 2-(3,4-Methylenedioxyphenyl)vinyl 1-ethylcyclopropyl ketone [III; Ar is 3,4-methylenedioxyphenyl, R is $C_2H_5$].

A mixture of 33.6 g. (0.3 mole) of 1-ethylcyclopropyl methyl ketone and 45 g. (0.3 mole) of piperonal in 21 ml. of ethanol was stirred at room temperature, and 21 ml. of 20% aqueous sodium hydroxide was added dropwise over a period of 30–45 minutes. The mixture was warmed at 40°–60° C. for three hours with stirring. The solution was then cooled to 0°–10° C., 0.2 ml. of glacial acetic acid added, and the mixture was extracted with ether. The ether extracts were concentrated, and the residue dissolved in 200 ml. of 95% ethanol, which solution when cooled caused separation of a solid product. The latter was recrystallized from 150 ml. of methanol to give 39 g. of 2-(3,4-methylenedioxyphenyl)vinyl 1-ethylcyclopropyl ketone, m.p. 62°–64° C.

A2. 2-(3,4-Methylenedioxyphenyl)vinyl cyclopropyl ketone [III; Ar is 3,4-methylenedioxyphenyl, R is H] was prepared from 8.4 g. of cyclopropyl methyl ketone and 15 g. of piperonal according to the procedure described above in Preparation A1 affording 21.5 g., m.p. 85°–87° C. when recrystallized from ethanol.

A3. 2-(3,4-Methylenedioxyphenyl)vinyl 1-methylcyclopropyl ketone [III; Ar is 3,4-methylenedioxyphenyl, R is $CH_3$] was prepared from 25.6 g. of 1-methylcyclopropyl methyl ketone and 39.3 g. of piperonal according to the procedure described above in Preparation A1, affording 29.5 g. of crystalline product.

A4. 2-(3,4-Dimethoxyphenyl)vinyl 1-ethylcyclopropyl ketone [III; Ar is 3,4-$(CH_3O)_2C_6H_3$, R is $C_2H_5$] was prepared from 22.4 g. of 1-ethylcyclopropyl methyl ketone and 33.2 g. of veratraldehyde according to the procedure described above in Preparation A1, affording 20.3 g., b.p. 156°–158° C. (0.02 mm.).

A5. 2-(4-Methoxyphenyl)vinyl cyclopropyl ketone [III; Ar is 4-$CH_3OC_6H_4$, R is H] was prepared from 84.1 g. of cyclopropyl methyl ketone and 136 g. of p-methoxybenzaldehyde according to the procedure described above in Preparation A1, affording 173.5 g., m.p. 70°–72° C. when recrystallized from ethanol.

A6. 2-Phenylvinyl cyclopropyl ketone [III; Ar is $C_6H_5$, R is H] was prepared from 13.5 g. of cyclopropyl methyl ketone and 17.1 g. of benzaldehyde according to the procedure described above in Preparation A1, affording 23.0 g., m.p. 58°–60° C. when recrystallized from absolute ethanol.

A7. 2-(4-Chlorophenyl)vinyl cyclopropyl ketone [III; Ar is 4-$ClC_6H_4$, R is H] was prepared from 25.2 g. of cyclopropyl methyl ketone and 42 g. of p-chlorobenzaldehyde according to the procedure described above in Preparation A1, affording 31 g., m.p. 63°–65° C. when recrystallized from ethanol.

A8. 2-(p-Tolyl)vinyl cyclopropyl ketone [III; Ar is 4-$CH_3C_6H_4$, R is H] was prepared from 84.1 g. of cyclopropyl methyl ketone in 120 g. of p-tolualdehyde according to the procedure described above in Preparation A1, affording 158.7 g., colorless plates, m.p. 78°–80° C. when recrystallized from ethanol.

A9. 2-(4-Carboxyphenyl)vinyl 1-ethylcyclopropyl ketone [III; Ar is 4-$HO_2CC_6H_4$, R is $C_2H_4$] was prepared from 67.2 g. of 1-ethylcyclopropyl methyl ketone and 90 g. of p-carboxybenzaldehyde according to the procedure described above in Preparation A1, affording 40 g., m.p. 183.5°–184.5° C. when recrystallized from acetonitrile and then repeatedly from isopropyl alcohol.

By following the procedure of Preparation A1 above, 1-isopropylcyclopropyl methyl ketone or 1-butylcyclopropyl methyl ketone can be caused to react with piperonal to give 2-(3,4-methylenedioxyphenyl)vinyl 1-isopropylcyclopropyl ketone [III; Ar is 3,4-methylenedioxyphenyl, R is $(CH_3)_2CH$], or 2-(3,4-methylenedioxyphenyl)vinyl 1-butylcyclopropyl ketone [III; Ar is 3,4-methylenedioxyphenyl, R is $CH_3CH_2CH_2CH_2$], respectively.

By following the procedure of Preparation A1 above, cyclopropyl methyl ketone can be caused to react with 3,4-dichlorobenzaldehyde, 2,4-dichlorobenzaldehyde, 4-bromobenzaldehyde, 4-fluorobenzaldehyde, 4-hydroxybenzaldehyde, 4-trifluoromethoxybenzaldehyde or 4-trifluoromethylbenzaldehyde to give, respectively, 2-(3,4-dichlorophenyl)vinyl cyclopropyl ketone [III; Ar is $3,4-Cl_2C_6H_3$, R is H], 2-(2,4-dichlorophenyl)vinyl cyclopropyl ketone [III; Ar is $2,4-Cl_2C_6H_3$, R is H], 2-(4-bromophenyl)vinyl cyclopropyl ketone [III; Ar is $4-BrC_6H_4$, R is H], 2-(4-fluorophenyl)vinyl cyclopropyl ketone [III; Ar is $4-FC_6H_4$, R is H], 2-(4-hydroxyphenyl)vinyl cyclopropyl ketone [III; Ar is $4-HOC_6H_4$, R is H], 2-(4-trifluoromethoxyphenyl)vinyl cyclopropyl ketone [III; Ar is $4-F_3COC_6H_4$, R is H], or 2-(4-trifluoromethylphenyl)vinyl cyclopropyl ketone [III; Ar is $4-F_3CC_6H_4$, R is H]. 2-(4-Hydroxyphenyl)vinyl cyclopropyl ketone can be esterified with benzoyl chloride to give 2-(4-benzoyloxyphenyl)vinyl cyclopropyl ketone [III; Ar is $4-C_6H_5COOC_6H_4$, R is H].

According to the procedures of Preparations A1–A9 using the appropriate starting materials, the following compounds were prepared:

A10. 2-(2,4-Dichlorophenyl)vinyl cyclopropyl ketone [III; Ar is $2,4-Cl_2C_6H_3$, R is H], yellow solid, m.p. 85°–87° C. (from isopropyl alcohol).

A11. 2-(4-Acetamidophenyl)vinyl cyclopropyl ketone [III; Ar is $4-CH_3CONHC_6H_4$, R is H], yellow crystals, m.p. 191°–192° C.

A12. 1-Cyclopropyl-5-(p-methoxyphenyl)-2,4-pentadien-1-one, $C_3H_5COCH=CHCH=CH-C_6H_4OCH_3-4$, yellow solid, m.p. 131°–132.5° C. (from ethanol) prepared from 4-methoxycinnamaldehyde and cyclopropyl methyl ketone.

A13. 2-(4-Dimethylaminophenyl)vinyl cyclopropyl ketone [III; Ar is $4-(CH_3)_2NC_6H_4$, R is H], yellow solid, m.p. 137°–139° C. (from ethanol), active against equine rhino virus in vitro at 12 micrograms per milliliter.

A14. 2-(4-Benzyloxyphenyl)vinyl cyclopropyl ketone [III; Ar is $4-C_6H_5CH_2OC_6H_4$, R is H], cream-colored solid, m.p. 111°–113° C. (from ethanol), active against equine rhino virus in vitro at 12 micrograms per milliliter.

A15. 2-(3,4-Dibenzyloxyphenyl)vinyl cyclopropyl ketone [III; Ar is $3,4-(C_6H_5CH_2O)_2C_6H_3$, R is H], cream-colored solid, m.p. 100°–102° C. (from methanol), active against equine rhino virus in vitro at 1.5 micrograms per milliliter.

A16. 2-(4-Trifluoromethoxyphenyl)vinyl cyclopropyl ketone [III; Ar is $4-F_3COC_6H_4$, R is H].

A17. 2-(1-Naphthyl)vinyl cyclopropyl ketone [III; Ar is 1-naphthyl, R is H].

A18. 2-(4-Fluorophenyl)vinyl cyclopropyl ketone [III; Ar is $4-FC_6H_4$, R is H].

A19. 2-(4-Diethylaminophenyl)vinyl cyclopropyl ketone [III; Ar is $4-(C_2H_5)_2NC_6H_4$, R is H], yellow solid, m.p. 79°–81° C. (from ethanol).

A20. 2-(4-Benzyloxy-3,5-dimethoxyphenyl)vinyl cyclopropyl ketone [III; Ar is $3,5-(CH_3O)_2-4-C_6H_5CH_2OC_6H_2$, R is H], light yellow crystals, m.p. 98°–99° C. (from ethanol).

A21. 2-(3-Iodo-4-methoxyphenyl)vinyl cyclopropyl ketone [III; Ar is $3-I-4-CH_3OC_6H_3$, R is H], light yellow solid, m.p. 89°–90° C., active against equine rhino virus in vitro at 6 micrograms per milliliter.

A22. 2-(4-Aminosulfonylphenyl)vinyl cyclopropyl ketone [III; Ar is $4-H_2NSO_2C_6H_4$, R is H], m.p. 173° C.

The foregoing intermediates of formula III were converted to final products of formula I as described in the copending parent application, Ser. No. 740,358, filed Nov. 10, 1976, now U.S. Pat. No. 4,093,736, the disclosure of which is incorporated herein by reference.

I claim:

1. A compound of the formula

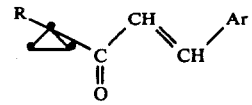

wherein R is hydrogen or lower-alkyl of 1 to 4 carbon atoms, and Ar is phenyl, naphthyl or phenyl substituted by 3,4-methylenedioxy or from one to three monovalent substituents selected from the group consisting of lower-alkyl of 1 to 4 carbon atoms, lower-alkoxy of 1 to 4 carbon atoms, halogen, trifluoromethyl, trifluoromethoxy, and benzyloxy.

2. 2-(4-Benzyloxyphenyl)vinyl cyclopropyl ketone, according to claim 1.

3. 2-(3,4-Dibenzyloxyphenyl)vinyl cyclopropyl ketone, according to claim 1.

4. 2-(2,4-Dichlorophenyl)vinyl cyclopropyl ketone, according to claim 1.

5. 2-(4-Benzyloxy-3,5-dimethoxyphenyl)vinyl cyclopropyl ketone, according to claim 1.

6. 2-(3-Iodo-4-methoxyphenyl)vinyl cyclopropyl ketone, according to claim 1.

7. 1-Cyclopropyl-5-(p-methoxyphenyl)-2,4-pentadien-1-one.

* * * * *